(12) United States Patent
Meng et al.

(10) Patent No.: US 10,898,428 B2
(45) Date of Patent: *Jan. 26, 2021

(54) PERSONAL CARE COMPOSITION

(71) Applicant: Conopco, Inc., Englewood Cliffs, NJ (US)

(72) Inventors: Sheng Meng, Shanghai (CN); Andrew Malcolm Murray, Neston (GB); Wenhui Song, Shanghai (CN); Su Yuan, Shanghai (CN); Wei Zhao, Shanghai (CN); Xiaoxia Yang, Shanghai (CN); Xiaoli Wang, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 118 days.

This patent is subject to a terminal disclaimer.

(21) Appl. No.: 16/305,512

(22) PCT Filed: May 22, 2017

(86) PCT No.: PCT/EP2017/062290
§ 371 (c)(1),
(2) Date: Nov. 29, 2018

(87) PCT Pub. No.: WO2017/211580
PCT Pub. Date: Dec. 14, 2017

(65) Prior Publication Data
US 2020/0163858 A1 May 28, 2020

(30) Foreign Application Priority Data
Jun. 10, 2016 (WO) ................. PCT/CN2016/085386
Jul. 18, 2016 (EP) ..................................... 16179928

(51) Int. Cl.
*A61K 8/891* (2006.01)
*C08L 83/14* (2006.01)
*A61K 8/58* (2006.01)
*A61Q 17/04* (2006.01)
*C08L 83/04* (2006.01)
*A61Q 19/00* (2006.01)
*C08G 77/00* (2006.01)

(52) U.S. Cl.
CPC .............. *A61K 8/891* (2013.01); *A61K 8/585* (2013.01); *A61Q 17/04* (2013.01); *C08L 83/04* (2013.01); *C08L 83/14* (2013.01); *A61K 2800/59* (2013.01); *A61Q 19/00* (2013.01); *C08G 77/80* (2013.01)

(58) Field of Classification Search
CPC ...................................................... C08G 77/80
See application file for complete search history.

(56) References Cited

U.S. PATENT DOCUMENTS

| | | | |
|---|---|---|---|
| 2005/0244351 A1 | 11/2005 | Reinhart et al. | |
| 2008/0206172 A1 | 8/2008 | Mohammadi et al. | |
| 2013/0045260 A1* | 2/2013 | Yamaguchi ............ | A61K 8/895 424/401 |
| 2013/0079368 A1* | 3/2013 | Omura .................. | A61Q 19/007 514/315 |
| 2014/0154294 A1* | 6/2014 | Finjan .................... | A61K 8/895 424/401 |
| 2016/0194455 A1 | 7/2016 | Mateu et al. | |

FOREIGN PATENT DOCUMENTS

| | | |
|---|---|---|
| FR | 2582313 | 11/1986 |
| JP | 2006213679 | 8/2006 |
| WO | WO9818849 | 5/1998 |
| WO | WO2007054492 | 5/2007 |
| WO | WO2013060559 | 5/2013 |
| WO | WO2014170865 | 10/2014 |
| WO | WO2014204937 | 12/2014 |

OTHER PUBLICATIONS

Search Report and Written Opinion in PCTEP2017062290; dated Sep. 28, 2017; World Intellectual Property Org. (WIPO)
Search Report and Written Opinion in EP16179928; dated Oct. 31, 2016; European Patent Office (EPO).
Search Report and Written Opinion EP16179937; dated Oct. 28, 2016.
Search Report and Written Opinion in PCTEP2017061001; dated Jul. 3, 2017.
Co-Pending Application entitled Personal Care Composition; Filed on Nov. 29, 2018.

* cited by examiner

*Primary Examiner* — Marc S Zimmer
(74) *Attorney, Agent, or Firm* — Ellen Plotkin

(57) ABSTRACT

A personal care composition is disclosed comprising a blend of silicone elastomer and solvent and a cosmetically acceptable carrier, wherein the solvent is a volatile silicone oil selected from octamethylcyclotetrasiloxane, decamethylcyclopentasiloxane, dodecamethylcyclohexasiloxane, blends of methyl trimethicone and dimethicone and mixtures thereof and wherein the silicone elastomer has the chemical structure of formula I. The composition may additionally optionally comprise an organic sunscreen. A method for providing skin care benefit, in particular photoprotection, comprises topically applying the composition to the skin.

16 Claims, No Drawings

PERSONAL CARE COMPOSITION

TECHNICAL FIELD OF THE INVENTION

The invention concerns a personal care composition, especially a personal care composition comprising silicone elastomer that has improved stability and good sensorial property.

BACKGROUND OF THE INVENTION

Silicone elastomers are extensively used in personal care products to provide desired sensorial properties. Silicone elastomer, as used herein, means cross-linked particles of a silicone polymer that swells significantly in a solvent forming a space filling material which behaves as a visco-elastic soft solid. Generally, the silicone elastomers are used in a blend of silicone elastomer and solvent, which is a dispersion of the silicone elastomer in the solvent. Most conventional silicone elastomers are siloxanes containing neither hydrophilic nor hydrophobic part, which leads to poor compatibility with many organic oils including organic sunscreen agents. Most conventional silicone elastomers can form gel with solvent however it is difficult to prepare a stable composition without any other thickener when adding it to the oil phase of the composition probably due to the poor compatibility of conventional silicone elastomers with organic oils. The structure of the blend of silicone elastomers and solvent may collapse which renders it ineffective in providing desired sensorial properties. The viscosity of composition will be decreased and eventually it will become unstable.

The present inventors have now found unexpectedly that functional silicone elastomers, which are silicone elastomers modified by grafting hydrophobic and/or hydrophilic groups onto the backbones of elastomers, present better structure benefit than conventional silicone elastomers. The functional silicone elastomers used in this invention are alkyl modified, phenyl modified and/or dual (alkyl and phenyl) modified silicone elastomers. Particularly, the dual (alkyl and phenyl) modified silicone elastomer shows the best structuring benefit, providing a personal care composition with enhanced stability and desired sensorial property.

Solar radiation includes ultraviolet (UV) radiation. Important ultraviolet wavelength regions are UV-A region from 320 to 400 nm and UV-B region from 290 to 320 nm. It is known that UV-B radiation is high energy emission that can cause significant damage to living tissues and cells, especially it is responsible for sunburn, melanoma and formation of wrinkles with prolonged and cumulative exposure. Recently, it is revealed that UV-A radiation also causes skin damage. UV-A radiation penetrates deeper into the skin than what is known earlier that can cause damage to the elastin fibers located deeper in the skin and thus hasten skin aging. Therefore, it is desirable for people to protect their skin from harmful UV-A and UV-B radiation. Generally, both UV-A and UV-B sunscreens are included in sunscreen compositions to provide protection over a broad range of UV radiation.

To provide sunscreen compositions having high sun protection factor (SPF) and UV-A protection factor (UVAPF), one way is to incorporate high levels of UV-A and UV-B sunscreens. However, it is difficult to obtain stable compositions when high levels of sunscreens are incorporated in a composition comprising silicone elastomers due to the poor compatibility between the two. The structure of the blend of silicone elastomer and solvent may collapse which render it ineffective in providing desired sensorial properties.

Additionally, the sunscreen composition may further comprise an emollient oil such as caprylic/capric triglycerides to act as a co-solvent for better dispersing UV-A sunscreen agents. However, caprylic/capric triglycerides is a bad solvent for silicone elastomers that will also cause the structure of the blend of silicone elastomer and solvent to collapse.

Different approaches were developed to improve the compatibility between silicone elastomers and organic oils, including optimizing solvent/elastomer blends, adding or changing the solvents, and/or adding modified polydimethicone polymer. However, these approaches do not provide satisfactory sensory and are cost ineffective.

It is of increasing interest to develop ways to stabilize sunscreen compositions comprising silicone elastomers that result in excellent sensory benefits.

The present inventors have now found unexpectedly that the compatibility between the silicone elastomers and organic oils can be improved by using functional silicone elastomers, which are silicone elastomers modified by grafting hydrophobic and/or hydrophilic groups onto the backbones of elastomers. The functional silicone elastomers used in this invention are alkyl modified, phenyl modified and/or dual (alkyl and phenyl) modified silicone elastomers. It has been found that the functional silicone elastomers showed improved compatibility with organic sunscreen agents. Particularly, the dual (alkyl and phenyl) modified silicone elastomer shows the best compatibility with organic sunscreen agents, providing a sunscreen composition with enhanced stability and desired sensorial property. Additionally, it has been also found unexpectedly that dual (alkyl and phenyl) modified silicone elastomer also showed excellent compatibility with emollient oils that act as co-solvents.

SUMMARY OF THE INVENTION

In a first aspect, the present invention is concerned with a personal care composition comprising:

i) a blend of silicone elastomer and solvent; and ii) a cosmetically acceptable carrier;

wherein the solvent is a volatile silicone oil selected from octamethylcyclotetrasiloxane, decamethylcyclopentasiloxane, dodecamethylcyclohexasiloxane, blends of methyl trimethicone and dimethicone and mixtures thereof; and wherein the silicone elastomer has the chemical structure of formula I, wherein:

each $R_1$ is independently $C_{4-36}$ alkyl chain, preferably $C_{8-18}$;

each $R_2$ is independently phenyl or $CH_3$;

each $R_3$ is independently phenyl; and each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500.

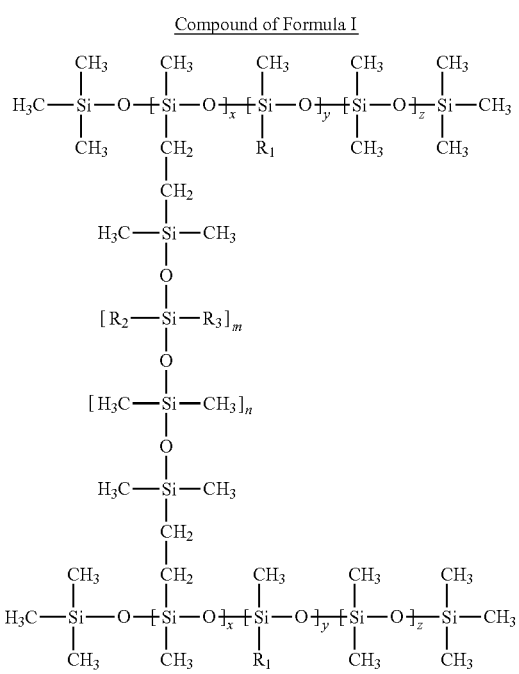

Compound of Formula I

In a second aspect, the present invention is directed to a packaged personal care product comprising the personal care composition of the first aspect of this invention.

In a third aspect, the present invention is directed to a method of using the personal care composition of any embodiment of the first aspect of this invention to provide skin care benefit.

All other aspects of the present invention will more readily become apparent upon considering the detailed description and examples which follow.

Except in the examples, or where otherwise explicitly indicated, all numbers in this description indicating amounts of material or conditions of reaction, physical properties of materials and/or use may optionally be understood as modified by the word "about".

All amounts are by weight of the final personal care composition, unless otherwise specified.

It should be noted that in specifying any ranges of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

Where a feature is disclosed with respect to a particular aspect of the invention (for example a composition of the invention), such disclosure is also to be considered to apply to any other aspect of the invention (for example a method of the invention) mutatis mutandis.

DETAILED DESCRIPTION

It has been found that functional silicone elastomers which are modified by alkyl, phenyl or dual (alkyl and phenyl) groups showed improved structuring benefit. Particularly, the dual (alkyl and phenyl) modified silicone elastomer shows the best structuring, providing a personal care composition with enhanced stability and desired sensorial property.

Now it has been also found that functional silicone elastomers which are modified by alkyl, phenyl or dual (alkyl and phenyl) groups showed improved compatibility with organic sunscreen agents. Particularly, the dual (alkyl and phenyl) modified silicone elastomer shows the best compatibility with organic sunscreen agents, providing a sunscreen composition with enhanced stability and desired sensorial property. Additionally, it has been found unexpectedly that dual (alkyl and phenyl) modified silicone elastomer also showed excellent compatibility with emollient oils that act as co-solvents.

Alkyl mole content as used herein, means the ratio of moles of alkyl substituted dimethicone units to the total moles of dimethicone units per mole of silicone elastomer unit, unless otherwise specified.

Phenyl mole content as used herein, means the ratio of moles of phenyl substituted dimethicone units to the total moles of dimethicone units per mole of silicone elastomer unit, unless otherwise specified.

By "A Personal Care Composition" as used herein, is meant to include a composition for topical application to the skin of mammals, especially humans. Such a composition may be generally classified as leave-on or rinse off but is preferably of the leave on type. The composition is formulated into a product which is applied to a human body specifically for improving appearance but may also be capable of providing cleansing, odor control or general aesthetics. The composition of the present invention can be in the form of a liquid, lotion, cream, foam, scrub, gel, or toner, or applied with an implement or via a face mask or a pad. Non-limiting examples of such compositions include leave-on skin lotions, creams, antiperspirants, deodorants, lipsticks, foundations, mascara, sunless tanners and sunscreen lotions. The composition of the present invention is preferably a leave-on composition. "Skin" as used herein is meant to include skin on the face and body (e.g., neck, chest, back, arms, underarms, hands, legs, buttocks and scalp) and especially to the sun exposed parts thereof.

"A Sunscreen Composition", as used herein, is meant to include a composition for topical application to sun-exposed areas of the skin and/or hair of mammals, especially humans. Such a composition may be generally classified as leave-on or rinse off, and includes any product applied to a human body for also improving appearance, cleansing, odor control or general aesthetics. It is preferably a leave-on product. The composition of the present invention can be in the form of a liquid, serum, lotion, cream, gel or toner, and may be applied with an implement or via a face mask, pad or patch. Preferably the composition is in the form of a lotion or cream. A particularly preferred example of such a composition is a leave-on skin cream. "Skin" as used herein is meant to include skin on the face and body (e.g. neck, chest, back, arms, underarms, hands, legs, buttocks and scalp) and especially to the sun exposed parts thereof. The composition of the invention is also of relevance to applications on any other keratinous substrates of the human body other than skin e.g. hair where products may be formulated with specific aim of providing photoprotection.

UV Sunscreen Agent

The composition of the invention comprises a UV-A sunscreen agent selected from the group consisting of a dibenzoylmethane derivative, a triazine derivative, a benzophenone derivative and mixtures thereof. In a preferred embodiment, the UV-A sunscreen agent comprises or is a dibenzoylmethane derivative, for example, butyl methoxydibenzoylmethane (sold under the trade name Parsol 1789).

As per a preferred aspect of the present invention the composition comprises 0.1 to 30% by weight of an organic sunscreen agent. Typically, the sunscreen composition of the present invention comprises from 0.1 to 15% by weight of the UV-A sunscreen agent, more preferably from 0.1 to 10%, most preferably from 1 to 5%, based on the total weight of the sunscreen composition and including all ranges subsumed therein.

The composition of the invention also comprises a UV-B sunscreen agent. Suitable UV-B sunscreen agent of the invention is selected from the group consisting of a benzophenone, an anthranilate, a salicylate, a cinnamate, a camphor, benzylidene malonate, a triazone, and derivatives thereof. In a preferred embodiment, the UV-B sunscreen agent comprises or is a cinnamate derivative, for example, ethylhexyl methoxycinnamate (sold under the trade name Parsol MCX).

Typically, the sunscreen composition of the present invention comprises from 0.1 to 20% by weight of the UV-B sunscreen agent, more preferably from 0.5 to 18%, most preferably from 1 to 15%, based on the total weight of the sunscreen composition and including all ranges subsumed therein.

As per an alternative aspect of the present invention the composition is substantially free of an organic sunscreen agent.

A Blend of Silicone Elastomer and Solvent

Silicone elastomer, as used herein, means cross-linked particles of a silicone polymer that swells significantly in a solvent forming a space filling material which behaves as a visco-elastic soft solid. Generally, the silicone elastomers are used in a blend of silicone elastomer and solvent, which is a dispersion of the silicone elastomer in the solvent. The blends of silicone elastomer and solvent are cross-linked gels that can be prepared through a hydrosilylation reaction. The reaction involves low levels of catalyst, usually platinum derivatives, and is generally run into an adequate solvent. Silicone-hydride (SiH) containing silicone polymers are reacted with di-vinyl materials to link independent silicone chains.

The solvent suitable for dispersing silicone elastomers is a low molecular weight linear or cyclic silicone oil. The elastomer can be swollen with the low molecular weight silicone oil under a shear force. The low molecular weight silicone oil is preferably a volatile oil, although non-volatile oils can also be used. The volatile silicone oil as per the present invention has a vapor pressure value at 25° C. of 2.6 to 1400 Pa. Particularly preferred volatile oils are linear siloxanes containing from 3 to 9 silicon atoms, and cyclic siloxanes having from 4 to 6 silicon atoms such as cyclopentasiloxane.

In a preferred embodiment, the solvent is a volatile silicone oil. Illustrative yet non-limiting examples of the types of volatile silicone oils that may be used in this invention as a solvent for silicone elastomers include, for example, hexamethylcyclotrisiloxane, octamethylcyclotetrasiloxane, decamethylcyclopentasiloxane, dodecamethylcyclohexasiloxane, blends of methyl trimethicone and dimethicone and mixtures thereof or the like. Examples of commercially available volatile silicone oils include oils having grade designations 344, 345, 244, 245 and 246 from Dow corning Corporation. In a preferred embodiment, the volatile silicone oil is decamethylcyclopentasiloxane, which is made commercially available, for example, from supplier like Dow Corning Corporation under the trade name DC245.

In a preferred embodiment, the blend of silicone elastomer and solvent is a blend of silicone elastomer and volatile silicone oil.

Typically, the blend of silicone elastomer and solvent comprises from 30% to 96% by weight of the solvent, more preferably from 50% to 94%, and most preferably from 67% to 92%.

Silicone elastomers suitable for use in the present invention are functional silicone elastomers that are modified by grafting functional groups onto the backbones of elastomers. In an especially preferred embodiment, the functional silicone elastomers used in this invention are alkyl modified, phenyl modified and/or dual (alkyl and phenyl) modified silicone elastomers.

Alkyl modified functional silicone elastomer may be prepared from the reaction of a) a silicone-hydride containing polysiloxane; b) an alkene; and c) a vinyl-terminated dimethylpolysiloxane by using a hydrosilylation catalyst.

The silicone-hydride containing polysiloxane has the general formula:

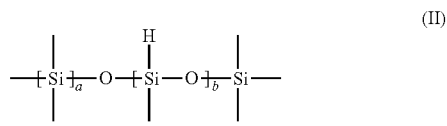

(II)

wherein:

each a is independently an integer from 0 to 300, preferably from 5 to 50; and each b is independently an integer from 2 to 300, preferably from 5 to 30;

Silicone-hydride content as used herein, means the moles of silicone-hydride groups per gram of polysiloxane. Typically, the silicone-hydride content of the polysiloxane ranges from 0.016 to 16.6 mM/g, more preferably from 1 to 10 mM/g, and most preferably from 3 to 8 mM/g, based on the total weight of the polysiloxane and including all ranges subsumed therein.

Additionally or alternatively, the silicone-hydride containing polysiloxane has a viscosity from 10 to 1000 centistokes (cSt), preferably from 20 to 500 cSt, more preferably from 25 to 150 cSt, and most preferably from 30 to 80 cSt.

Suitable silicone-hydride containing polysiloxanes which are commercially available include Andisil XL-10, Andisil XL-11, Andisil XL-15 from AB Specialty Silicones.

The alkene is an unsaturated hydrocarbon that contains at least one carbon-carbon double bond. Alkenes have two hydrogen atoms less than the corresponding alkane (with the same number of carbon atoms) with the general formula $C_nH_{2n}$. Preferably, the alkene suitable for use in the reaction has carbon chain lengths ranging from $C_8$ to $C_{18}$. Illustrative yet non-limiting examples of the alkenes that may be used in this reaction include, for example, octene, nonene, decene, undecene, dodecene, tridecene, tetradecene, pentadecene, hexadecene, heptadecene, octadecene or mixtures thereof. Preferably, the alkene is octene, dodecene, hexadecene or mixtures thereof.

The vinyl-terminated dimethylpolysiloxane has the general formula:

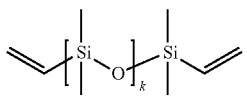

(III)

wherein:

each k is independently an integer from 4 to 1000, preferably from 40 to 500.

The vinyl-terminated dimethylpolysiloxane contains vinyl side groups which may be available for reaction with silicone-hydride containing polysiloxane.

Vinyl content as used herein, means the moles of vinyl group per gram of the vinyl-terminated dimethylpolysiloxane. Typically, the vinyl content of the vinyl-terminated dimethylpolysiloxane ranges from 0.05 to 3 mM/g, more preferably from 0.1 to 1 mM/g, and most preferably from 0.2 to 0.8 mM/g, based on the total weight of the vinyl-terminated dimethylpolysiloxane and including all ranges subsumed therein.

Additionally or alternatively, the vinyl-terminated dimethylpolysiloxane has a viscosity from 10 to 1000 cSt, preferably from 20 to 500 cSt, more preferably from 50 to 400 cSt and most preferably from 100 to 250 cSt.

Suitable vinyl-terminated dimethylsiloxanes which are commercially available include Andisil VS-200 from AB Specialty Silicones.

In the reaction, the alkene reacts with the silicone-hydride containing polysiloxane to form an alkyl modified polysiloxane, which reacts with the vinyl-terminated dimethylpolysiloxane to form the alkyl modified silicone elastomer.

The alkyl mole content of the alkyl modified silicone elastomer is typically in the range from 0.01 to 0.99, more preferably from 0.02 to 0.20.

In a preferred embodiment, the alkyl modified functional silicone elastomer has the general formula:

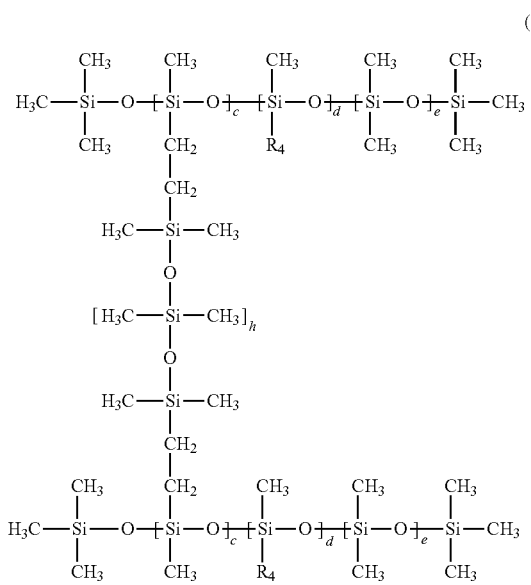

(IV)

wherein:

each $R_4$ is independently $C_{4-36}$ alkyl chain, preferably $C_{8-18}$; and each c is independently an integer from 3 to 100, preferably from 3 to 20; each d is independently an integer from 1 to 100, preferably from 1 to 20; each e is independently an integer from 1 to 100, preferably from 6 to 50; and each h is independently an integer from 4 to 1000, preferably from 40 to 500.

Phenyl modified functional silicone elastomer may be prepared from the reaction of a) a silicone-hydride containing polysiloxane; and b) a vinyl-terminated dimethyl phenyl polysiloxane by using a hydrosilylation catalyst.

The silicone-hydride containing polysiloxane is the same as described above.

The vinyl-terminated dimethyl phenyl polysiloxane has the general formula:

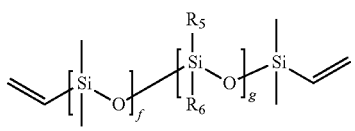

(V)

wherein:

each $R_5$ is independently phenyl or $CH_3$;

each $R_6$ is independently phenyl; and each f is independently an integer from 4 to 1000, preferably from 40 to 500; and each g is independently an integer from 1 to 100, preferably from 5 to 30.

The vinyl-terminated dimethyl phenyl polysiloxane contains vinyl side groups which may be available for reaction with silicone-hydride containing polysiloxane.

Phenyl mole content as used herein, means the ratio of moles of phenyl substituted dimethicone units to the total moles of dimethicone units of the vinyl-terminated dimethyl phenyl polysiloxane. Typically, the phenyl mole content of the vinyl-terminated dimethyl phenyl polysiloxane ranges from 1 to 50%, more preferably from 3 to 30% and most preferably from 7 to 15%.

Additionally or alternatively, the vinyl-terminated dimethyl phenyl polysiloxane has a viscosity from 100 to 10000 cSt, preferably from 500 to 8000 cSt, more preferably from 800 to 5000 cSt and most preferably from 1000 to 2000 cSt.

Suitable vinyl-terminated dimethyl phenyl polysiloxane which are commercially available include Andisil SF-2430 from AB Specialty Silicones.

Preferably, the silicone-hydride containing polysiloxane and the vinyl-terminated dimethyl phenyl polysiloxane are present in the reaction mixture in a weight ratio from 1:200 to 200:1, more preferably from 1:50 to 50:1, most preferably from 1:30 to 30:1.

The phenyl mole content of the phenyl modified silicone elastomer is typically in the range from 0.01 to 0.50, preferably from 0.03 to 0.34.

In a preferred embodiment, the phenyl modified functional silicone elastomer has the general formula:

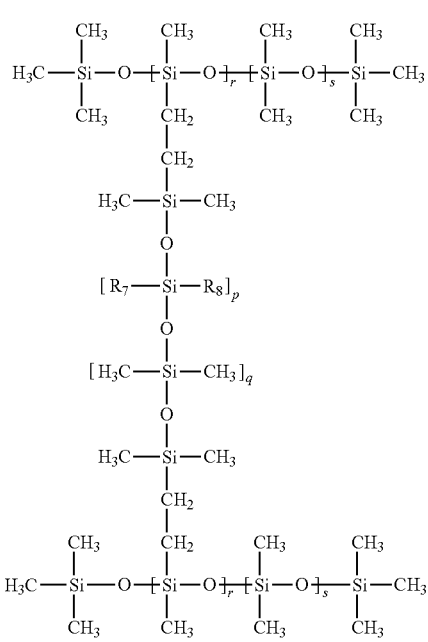

(VI)

wherein:
each $R_7$ is independently phenyl or $CH_3$;
each $R_8$ is independently phenyl; and
each r is independently an integer from 3 to 100, preferably from 3 to 20; each s is independently an integer from 2 to 200, preferably from 7 to 70; each p is independently an integer from 1 to 100, preferably from 5 to 30; and each q is independently an integer from 4 to 1000, preferably from 40 to 500.

Dual (alkyl and phenyl) modified silicone elastomer may be prepared from the reaction of a) a silicone-hydride containing polysiloxane; b) an alkene; and c) a vinyl-terminated dimethyl phenyl polysiloxane by using a hydrosilylation catalyst.

The silicone-hydride containing polysiloxane, the alkene and the vinyl-terminated dimethyl phenyl polysiloxane are the same as described above.

The dual modified silicone elastomer may be prepared through a two-step synthesis by combining the reactants. In the first step, the alkene reacts with the silicone-hydride containing polysiloxane to form an alkyl modified polysiloxane. In the second step, the left unsubstituted silicone-hydride groups on the alkyl modified polysiloxane react with the vinyl side groups on the vinyl-terminated dimethyl phenyl polysiloxane to form the dual modified silicone elastomer.

For the first step, the temperature of the reaction mixture may be any suitable temperature at which the silicone-hydride containing polysiloxane and the alkene can react to form the alkyl modified polysiloxane. Preferably the temperature of the reaction mixture is from 5° C. to 100° C., more preferably from 10° C. to 80° C. and most preferably from 20° C. to 60° C.

The reaction time for the first step is at least 5 mins, more preferably at least 10 mins, most preferably from 20 to 60 mins.

For the second step, the temperature of the reaction mixture may be any suitable temperature at which the alkyl modified polysiloxane and the vinyl-terminated dimethyl phenyl polysiloxane can react to form the dual modified silicone elastomer. Preferably the temperature of the reaction mixture is from 10° C. to 120° C., more preferably from 20° C. to 100° C. and most preferably from 40° C. to 80° C.

The reaction time for the second step is at least 1 hour, more preferably at least 2 hours, most preferably from 3 hours to 6 hours.

The alkyl mole content of the dual (alkyl and phenyl) modified silicone elastomer is typically in the range from 0.01 to 0.99, more preferably from 0.02 to 0.20.

The phenyl mole content of the dual (alkyl and phenyl) modified silicone elastomer is typically in the range from 0.01 to 0.50, preferably from 0.03 to 0.34.

In a preferred embodiment, the dual (alkyl and phenyl) modified silicone elastomer has the general formula:

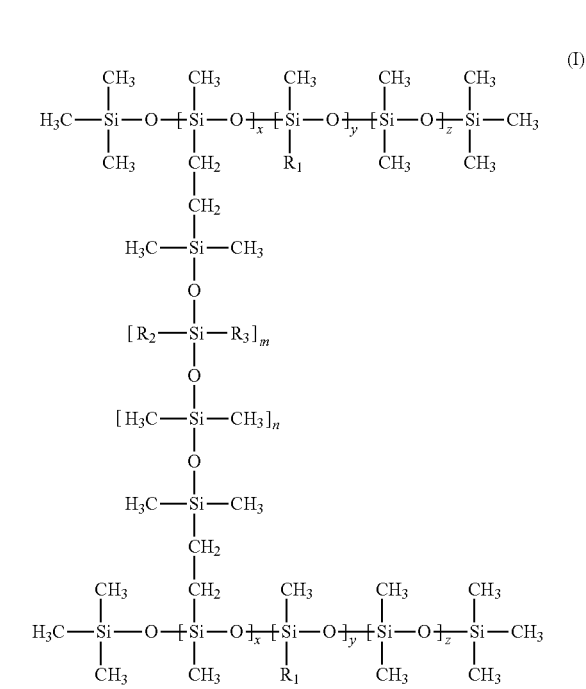

(I)

wherein:
each $R_1$ is independently $C_{4-36}$ alkyl chain, preferably $C_{8-18}$;
each $R_2$ is independently phenyl or $CH_3$;
each $R_3$ is independently phenyl; and
each x is independently an integer from 3 to 100, preferably from 3 to 20; each y is independently an integer from 1 to 100, preferably from 1 to 20; each z is independently an integer from 1 to 100, preferably from 6 to 50; each m is independently an integer from 1 to 100, preferably from 5 to 30; and each n is independently an integer from 4 to 1000, preferably from 40 to 500.

Typically, the blend of silicone elastomer and solvent preferably comprises from 1 to 70% by weight of silicone elastomer, more preferably from 5 to 50%, and most preferably from 8 to 30%.

The blend of silicone elastomer and solvent preferably comprises the silicone elastomer and the solvent in a weight ratio from 1:20 to 2:1, more preferably from 1:15 to 1:1, and most preferably from 1:11 to 1:2.

Typically, the personal care composition of the present invention comprises the blend of silicone elastomer and solvent in an amount of from 0.1 to 60%, more preferably from 1 to 40%, most preferably from 5 to 30%, based on the total weight of the personal care composition and including all ranges subsumed therein.

Other Components

The personal care composition of the present invention may further comprise an emollient oil that act as a co-solvent. Suitable emollient oils include, for example, ester of alkoxylated aromatic alcohol with fatty carboxylic acid, esters of polyglycols or diols with fatty carboxylic acid such as caprylic/capric triglyceride, ester of fatty alcohol and fatty acid, alkoxylated derivative of benzyl alcohol and mixtures thereof. Preferably the emollient oil is caprylic/capric triglyceride.

Typically, the personal care composition of the present invention comprises co-solvent in an amount from 0.01 to 10%, more preferably from 0.1 to 8%, most preferably from 1 to 6%, based on the total weight of the personal care composition and including all ranges subsumed therein.

The personal care composition of the invention comprises a cosmetically acceptable carrier. The carrier may be a liquid or solid material. Typically, carrier is present in an amount ranging from 10 to 99.9%, more preferably from 20 to 95%, most preferably from 40 to 85% by total weight of the personal care composition including all ranges subsumed therein. It is particularly preferred that the cosmetically acceptable carrier includes water. Water is preferably included in an amount from 30 to 90%, more preferably from 30 to 85%, most preferably from 30 to 80% by total weight of the personal care composition. Besides water, suitable carrier classes include silicones, polyhydric alcohols, hydrocarbons, triglycerides and thickening powders.

The personal care composition of the invention may be in any form including toners, lotions, creams, mousses, scrub, serum or gel that is suitable for topical application to the skin. The personal care composition can be either a leave-on product such as skin lotions, creams, antiperspirants, deodorants, lipsticks, foundations, mascara, sunless tanners and sunscreen lotions or a rinse-off product such as shampoos, conditioners, shower gels and toilet bars. It is preferred that the personal care composition is a skin lotion or a cream.

The personal care composition may additionally comprise other sunscreen agents such as inorganic sunscreens. For example, zinc oxide, titanium dioxide, iron oxide, silica such as fumed silica. The amount of such sunscreen agents is preferably incorporated from 0.1 to 5% by total weight of the personal care composition.

A skin lightening agent may also be incorporated into the composition of the invention. Suitable skin lightening agents include vitamin B3 and its derivatives (e.g. niacin, nicotinic acid, niacinamide), kojic acid, arbutin, tranexamic acid, placental extract, ascorbic acid and its derivatives (e.g. magnesium ascorbyl phosphate, sodium ascorbyl phosphate, ascorbyl glucoside, and ascorbyl tetraisopalmitates), aloe extract, ammonium lactate, azelaic acid, citrate esters, ellagic acid, glycolic acid, green tea extract, hydroquinone, lemon extract, linoleic acid, vitamins like vitamin B6, vitamin B12, vitamin C, vitamin A, a dicarboxylic acid, resorcinol derivatives, hydroxycarboxylic acid like lactic acid and their salts (e.g. sodium lactate) or a mixture thereof. Most preferred is niacinamide. Typically the skin lightening agent is present in an amount from 0.1 to 10%, more preferably from 0.2 to 5%, most preferably from 0.3 to 3% by total weight of the personal care composition including all ranges subsumed therein.

The personal care composition may also comprise other ingredients which are common in the art to enhance physical properties and performance. Suitable ingredients include but are not limited to humectants, thickeners, opacifiers, binders, colorants and pigments, pH adjusting agents, preservatives, optics, perfumes, viscosity modifiers, biological additives, buffering agents, conditioners, natural extracts, essential oils and skin benefit agents including anti-inflammatory agents, cooling agents, antiperspirant agents, anti-aging agents, anti-acne agents, anti-microbial agents and antioxidants.

The invention is further concerned with a method of using the personal care composition to provide enhanced skin care benefit.

The following examples are provided to facilitate an understanding of the present invention. The examples are not provided to limit the scope of the claims.

EXAMPLES

Example 1

This example demonstrates the structuring benefit of functional silicone elastomers. The base formulation used is listed in table 1. All ingredients are expressed by weight percent by the total formulation, and as level of active ingredient.

TABLE 1

| Ingredient | Percent by weight |
| --- | --- |
| DC245[a] | Balance |
| Silicone elastomer/DC245 blend[b] | Table 2 |
| PEG-10 dimethicone | 1.19 |
| Cholesterol | 0.20 |
| Stearic acid | 0.25 |
| Cetyl alcohol | 0.01 |
| Sucrose distearate | 0.13 |
| Thickener | Table 2 |
| Water | 46.38 |
| Glycerine | 7.25 |
| Disodium EDTA | 0.05 |
| Potassium chloride | 1.00 |
| Magnesium sulfate, heptahydrate | 0.50 |
| Niacinamide | 3.00 |
| Carprylic/Capric Triglyceride/E | 8.5 |

[a]DC245 is a commercial decamethylcyclopentasiloxane from Dow Corning.
[b]Silicone elastomer/DC245 blend is selected from in-house prepared non-functional silicone elastomer (NSE)/DC245 blend and dual modified (alkyl and phenyl) silicone elastomer (DSE)/DC245 blend.

Preparation of Blends of Silicone Elastomer and Solvent Materials

Silicone-hydride containing polysiloxane (Andisil XL-10), vinyl-terminated dimethylpolysiloxane (Andisil VS-200), vinyl-terminated dimethyl diphenyl polysiloxane (Andisil SF-2430) were purchased from AB Specialty Silicones. Decamethylcyclopentasiloxane (DC245) was purchased from Dow Corning Corporation. Platinum catalyst is platinum (0)-1,3-divinyl-1,1,3,3-tetramethyldisiloxane complex solution-in xylene from Sigma Aldrich. All the chemicals were used as received without further purification.

Solid content, as used herein, refers to the weight percentage of silicone elastomers in the blend of silicone elastomer and solvent.

Non-Functional Silicone Elastomer/DC245 Blend 0.382 g Andisil XL-10, 12 g Andisil VS-200 and 70 g DC245 were mixed in a flask. 25 μL of platinum complex catalyst was added and the reaction mixture was kept at 45° C. with the reflux of water and stirred at 200 rpm for 5 hours.

The gelled mixture can be diluted to different solid content at 45° C. after the reaction was completed.

Dual Modified Silicone Elastomer/DC245 Blend 1.02 g Andisil XL-10, 0.94 g dodecene and 4 g DC245 were mixed and stirred in a vial, followed by the addition of 2 μL platinum complex catalyst. The mixture was stirred at 60° C. for 30 mins. Then the reaction mixture was transferred to a flask. 40 g DC245, 20 g Andisil SF-2430 and 6 μL platinum complex catalyst were added to the mixture and the mixture was kept at 60° C. with the reflux of water and stirred at 200 rpm for 4 hours. The gelled mixture can be diluted to different solid content at 60° C. after the reaction was completed.

Methods

The gelled mixtures (blends of silicone elastomer and solvent) were diluted to a solid content of 14.5%. Samples were prepared by adding different blends of silicone elastomer and solvent of the same amount and different amounts of thickener agent in the base formulation.

Viscosity Test

DV-II+ PRO Digital Viscometer (from Brookfield Ltd) was used to measure the viscosities of the samples with the needle of TD at a consistent shear rate of 5 rpm. This viscometer was connected with PC where an automated program can control the measurement. The values measured after 30 seconds at a temperature of 25° C. were used. Values are quoted in centipoises (cP=mPa·S) unless otherwise specified.

Stability Test

Stability, as used herein, refers to the composition maintaining its appearance, odor and main structure without phase separation. Samples were poured into plastic bottles and filled up to ⅔ of the bottles. Then the samples were stored at 50° C. in an oven. For stability test, samples were checked daily. The appearance of samples were observed and recorded. The observation was taken when the samples were still warm and then the samples were left in the oven for 24 hours before another observation was taken.

Amplitude Sweep Rheology Analysis

In amplitude sweep rheology test, the storage modulus and loss modulus represent the viscoelastic property. Normally, the storage modulus (initial G') represents the elasticity. In general, for in-house silicone elastomers, the acceptable range of the storage modulus (initial G') was from 800 Pa to 4000 Pa in personal care application.

The results of viscosity, rheology and stability are reported in table 2.

TABLE 2

| Samples | Silicone elastomer/DC245 blend | | Thickener Hectorite | Viscosity/cP | G' | Stability 4 weeks at 50° C. |
|---|---|---|---|---|---|---|
| | NSE (12.5%) | DSE (14.5%) | | | | |
| 1 | 26.5% | | 0.27% | 51760 | 1870 | Stable |
| 2 | | 12.7% | 0.27% | 44240 | 1270 | Stable |
| 3 | | 15.9% | 0.27% | 61440 | 1600 | Stable |

Results

It can be seen that in order to get the formulation with similar viscosity, elasticity and stability, more non-functional silicone elastomer has to be added compared to the dual functional elastomer. Dual modified silicone elastomer thus showed better structuring benefit.

Example 2

This example demonstrates the structuring benefit of functional silicone elastomers with the presence of an organic sunscreen agent. The base formulation used is listed in table 3. All ingredients are expressed by weight percent by the total formulation, and as level of active ingredient.

TABLE 3

| Ingredient | Percent by weight |
|---|---|
| DC245[a] | Balance |
| Silicone elastomer/DC245 blend[b] | Table 4 |
| PEG-10 dimethicone | 1.19 |
| Parsol MCX[c] | 6 |
| Cholesterol | 0.20 |
| Titanium dioxide | 2 |
| Mica &Titanium dioxide | 0.5 |
| Stearic acid | 0.25 |
| Cetyl alcohol | 0.01 |
| Sucrose distearate | 0.13 |
| Thickener | Table 4 |
| Water | 46.38 |
| Glycerine | 7.25 |
| Disodium EDTA | 0.05 |
| Potassium chloride | 1.00 |
| Magnesium sulfate, heptahydrate | 0.50 |
| Niacinamide | 3.00 |
| DMDM hydantion (and) iodopropynyl butylcarbamate | 0.2 |

[a]DC245 is a commercial decamethylcyclopentasiloxane from Dow Corning.
[b]Silicone elastomer/DC245 blend is selected from in-house prepared non-functional silicone elastomer (NSE)/DC245 blend and dual modified (alkyl and phenyl) silicone elastomer (DSE)/DC245 blend.
[c]Parsol MCX is ethylhexyl methoxycinnamate.

Methods

The same protocol was used to measure the viscosity and stability of the compositions as described in Example 1. Results are reported in table 4.

TABLE 4

| Samples | Silicone elastomer/DC245 blend | | Thickener Hectorite | Viscosity/cP | Stability 4 weeks at 50° C. |
|---|---|---|---|---|---|
| | NSE (12.5%) | DSE (14.5%) | | | |
| 4 | 26.5% | | 0.27% | 62400 | Stable |
| 5 | | 12.7% | 0.27% | 60560 | Stable |
| 6 | | 15.9% | | 68880 | Stable |

Results

It can be seen that in order to get the formulation with similar viscosity, elasticity and stability, more non-functional silicone elastomer has to be added compared to dual functional elastomer. Dual modified silicone elastomer thus showed better structuring benefit with the existence of organic sunscreen agent.

Sensory Testing

The sensorials delivered by the composition of the invention was compared to that of a composition outside the invention in a QDA (qualitative descriptive analysis) test. The evaluation was done by trained female respondents with good sensitivity.

The following attributes were scored during the various stages of the sample testing: Before use—appearance and fingertips: Integrity of shape, Firmness, Stringiness, Peaking, Stickiness In use/after use immediately (IMD): Spreadability, Thickness, Oily, Drag IMD, and Oily IMD After use IMD/5 min: Silky smooth IMD, Sticky tacky IMD, Drag 5 min, Oily 5 min, Silky smooth 5 min, Sticky tacky 5 min When a QDA test with Sample 4 was compared with Sample 5 and 6, it was found that there is no significant difference between the two samples in all of the above attributes in all of the various stages mentioned above. The data from the QDA test indicates that the composition with lower dosage of dual functional elastomer as per the invention (Sample 5 and 6) has comparable sensorials when in use as compared to a conventional composition with higher dosage of non-functional silicone elastomer (Sample 4).

Example 3

This example demonstrates the compatibility of silicone elastomers and organic sunscreen agents. The base formulation used is listed in table 5. All ingredients are expressed by weight percent by the total formulation, and as level of active ingredient.

TABLE 5

| Ingredient | Percent by weight |
| --- | --- |
| DC245[a] | Balance |
| Silicone elastomer/DC245 blend[b] | 26.5 |
| PEG-10 dimethicone | 1.19 |
| Parsol MCX[c] | Variant |
| Cholesterol | 0.20 |
| Stearic acid | 0.25 |
| Cetyl alcohol | 0.01 |
| Sucrose distearate | 0.13 |
| Water | 46.38 |
| Glycerine | 7.25 |
| Disodium EDTA | 0.05 |
| Potassium chloride | 1.00 |
| Magnesium sulfate, heptahydrate | 0.50 |
| Niacinamide | 3.00 |
| DMDM hydantion (and) iodopropynyl butylcarbamate | 0.20 |

[a]DC245 is a commercial decamethylcyclopentasiloxane from Dow Corning.
[b]Silicone elastomer/DC245 blend is selected from in-house prepared non-functional silicone elastomer (NSE)/DC245 blend, alkyl modified silicone elastomer (ASE)/DC245 blend, phenyl modified silicone elastomer (PSE)/DC245 blend and dual modified (alkyl and phenyl) silicone elastomer (DSE)/DC245 blend.
[c]Parsol MCX is ethylhexyl methoxycinnamate.

Preparation of Blends of Silicone Elastomer and Solvent

Materials

Silicone-hydride containing polysiloxane (Andisil XL-10), vinyl-terminated dimethylpolysiloxane (Andisil VS-200), vinyl-terminated dimethyl diphenyl polysiloxane (Andisil SF-2430) were purchased from AB Specialty Silicones. Decamethylcyclopentasiloxane (DC245) was purchased from Dow Corning Corporation.

Platinum catalyst is platinum (0)-1,3-divinyl-1,1,3,3-tetramethyldisiloxane complex solution-in xylene from Sigma Aldrich. All the chemicals were used as received without further purification.

Solid content, as used herein, refers to the weight percentage of silicone elastomers in the blend of silicone elastomer and solvent.

Non-Functional Silicone Elastomer/DC245 Blend 0.382 g Andisil XL-10, 12 g Andisil VS-200 and 70 g DC245 were mixed in a flask. 25 µL of platinum complex catalyst was added and the reaction mixture was kept at 45° C. with the reflux of water and stirred at 200 rpm for 5 hours. The gelled mixture can be diluted to different solid content at 45° C. after the reaction was completed.

Alkyl Modified Silicone Elastomer/DC245 Blend 1.068 g Andisil XL-10 and 23 g DC245 were mixed and stirred in a vial. 1.1 g isooctene was added into the mixture, followed by the addition of 10 µL platinum complex catalyst. The mixture was stirred at room temperature for 30 mins. Then the reaction mixture was transferred to a flask. 23 g DC245 and 20 g Andisil VS-200 were added into the mixture and then the mixture was kept at 45° C. with the reflux of water and stirred at 200 rpm. 15 µl of platinum complex catalyst was added and the reaction mixture was stirred at 45° C. for 5 hours. The gelled mixture can be diluted to different solid content at 45° C. after the reaction was completed.

Phenyl Modified Silicone Elastomer/DC245 Blend 0.6 g Andisil XL-15, 14 g Andisil SF-2430 and 70 g DC245 were mixed and stirred in a vial, followed by the addition of 25 µL platinum complex catalyst. The mixture was kept at 60° C. with the reflux of water and stirred at 200 rpm for 4 hours. The gelled mixture can be diluted to different solid content at 60° C. after the reaction was completed.

Dual Modified Silicone Elastomer/DC245 Blend 1.02 g Andisil XL-10, 0.94 g dodecene and 4 g DC245 were mixed and stirred in a vial, followed by the addition of 2 µL platinum complex catalyst. The mixture was stirred at 60° C. for 30 mins. Then the reaction mixture was transferred to a flask. 40 g DC245, 20 g Andisil SF-2430 and 6 µL platinum complex catalyst were added to the mixture and the mixture was kept at 60° C. with the reflux of water and stirred at 200 rpm for 4 hours. The gelled mixture can be diluted to different solid content at 60° C. after the reaction was completed.

Methods

The gelled mixtures (blends of silicone elastomer and solvent) were diluted to a solid content of 14.5%. Samples were prepared by adding different blends of silicone elastomer and solvent of the same amount and different amounts of sunscreen agent Parsol MCX in the base formulation. Sample 1 comprised non-functional silicone elastomer (NSE). Sample 2 comprised alkyl modified silicone elastomer (ASE). Sample 3 comprised phenyl modified silicone elastomer (PSE). Sample 4 comprised dual modified (alkyl and phenyl) silicone elastomer (DSE).

Viscosity Test

DV-II PRO Digital Viscometer (from Brookfield Ltd) was used to measure the viscosities of the roll on samples at a consistent shear rate of 10 rpm. This viscometer was connected with PC where an automate program can control the measurement. The values measured after 1 min at a temperature of 25° C. was used. Values are quoted in centipoises (cP=mPa·S) unless otherwise specified.

Stability Test

Stability, as used herein, refers to the composition maintaining its appearance, odor and main structure without phase separation. Samples were poured into plastic bottles and filled up to ⅔ of the bottles. Then the samples were stored at 50° C. in an oven. For stability test, samples were checked daily. The appearance of samples were observed and recorded. The observation was taken when the samples were still warm and then the samples were left in the oven for 24 hours before another observation was taken.

The results of viscosity and stability are reported in Table 6.

TABLE 6

| % Parsol MCX in total formulation | Samples | | | |
| --- | --- | --- | --- | --- |
| | 7 (NSE) | 8 (PSE) | 9 (ASE) | 10 (DSE) |
| 10 Viscosity/cP | 3280 | 15440 | 3760 | 19280 |
| Stability | Good stability for at least four weeks | | | |
| 12 Viscosity/cP | 3680 | 16320 | 3600 | 12560 |
| Stability | Unstable after three weeks | Good stability for at least four weeks | | |

TABLE 6-continued

| % Parsol MCX in total | Samples | | | |
|---|---|---|---|---|
| | formulation | 7 (NSE) | 8 (PSE) | 9 (ASE) | 10 (DSE) |
| 15 | Viscosity/cP | NM[d] | 1440 | 2400 | 1760 |
| | Stability | NM[d] | Unstable after three weeks | Unstable after three weeks | Good stability for at least four weeks |

[d]NM means that the data is not measured.

Results

It can be seen that Sample 7 comprising non-functional silicone elastomer showed bad compatibility with sunscreen agents. When sunscreen agents were added in an amount higher than 10 wt %, the formulation became unstable with slightly oil leakage. Sample 10 comprising dual modified silicone elastomer showed the best compatibility with sunscreen agents among all the samples. The formulation maintained good stability even when 15 wt % of sunscreen agents were added.

Example 4

This example demonstrates the sunscreen performance of the compositions. Samples used here were Samples 7 to 10 as listed in Example 3.

Methods

In Vitro SPF Test

Thin film transmittance measurements were carried out using LabSphere UV-2000S SPF meter. Poly(methyl methacrylate) (PMMA) plates were used as substrates. Samples were uniformly applied onto the PMMA substrates with a density of 2 mg/cm². After drying for 15 mins, the sample plates were exposed under standard UV lamp and transmittance scan was carried out for the sample plates. Nine different spots were scanned for each sample plate. The same sample was tested three times. The reference transmittance was obtained using a blank PMMA plate coated with glycerine with a density of 1.3 mg/cm². The transmittance values were converted to SPF values using the LabSphere software provided with the instrument.

The SPF values of samples of different combinations of silicone elastomers and sunscreen agents were measured and summarized in Table 7.

TABLE 7

| | % Parsol MCX in total | Samples | | |
|---|---|---|---|---|
| In vitro SPF | formulation | 7 (NSE) | 9 (ASE) | 10 (DSE) |
| | 10 | 10.00 | NM[d] | 11.19 |
| | 12 | 10.64 | 11.08 | 14.00 |
| | 15 | NM[d] | 14.04 | 17.24 |

TABLE 8

| Sample 4 (DSE) | % Parsol MCX in total formulation | In vitro SPF |
|---|---|---|
| | 6 | 7.40 |
| | 8 | 8.81 |
| | 10 | 11.19 |
| | 12 | 14.00 |
| | 15 | 17.24 |
| | 20 | 19.55 |

Results

It is demonstrated that even with the same amount of sunscreen agents, Sample 10 comprising dual modified silicone elastomer provides higher SPF values compared to Samples 7 and 9. Table 4 further showed that the SPF values of Sample 10 increased with an increase of the amount of sunscreen agents in the formulation.

Example 5

This example demonstrates the photo stability of compositions comprising dual modified (alkyl and phenyl) silicone elastomer. All ingredients are expressed by weight percent by the total formulation, and as level of active ingredient.

TABLE 9

| | Samples | |
|---|---|---|
| Ingredient | 11 | 12 |
| DC245[a] | Balance | Balance |
| Non-functional silicone elastomer/DC245 blend | 26.5 | — |
| Dual modified silicone elastomer/DC245 blend | — | 26.5 |
| PEG-10 dimethicone | 1.19 | 1.19 |
| Parsol MCX[c] | 5 | 5 |
| Parsol 1789[e] | 1 | 1 |
| Cholesterol | 0.20 | 0.20 |
| Stearic acid | 0.25 | 0.25 |
| Cetyl alcohol | 0.01 | 0.01 |
| Sucrose distearate | 0.13 | 0.13 |
| Water | 46.38 | 46.38 |
| Glycerine | 7.25 | 7.25 |
| Disodium EDTA | 0.05 | 0.05 |
| Potassium chloride | 1.00 | 1.00 |
| Magnesium sulfate, heptahydrate | 0.50 | 0.50 |
| Niacinamide | 3.00 | 3.00 |
| DMDM hydantion (and) iodopropynyl butylcarbamate | 0.20 | 0.20 |
| In vitro SPF   1 day storage | 5.25 | 5.57 |
|                24 days storage | 3.65 | 5.44 |

[e]Parsol 1789 is butyl methoxydibenzoylmethane.

Methods

Samples were prepared by adding different blends of silicone elastomer and solvent (with a solid content of 14.5%) of the same amount in the formulation. The same protocol was used to measure the in vitro SPF values of the compositions as described in Example 4.

Results

The results showed that Sample 12 comprising dual modified silicone elastomer maintained SPF values even after 24 days storage while the SPF values of Sample 11 decreased over time.

Example 6

This example demonstrates the effect of the concentration of a blend of dual modified silicone elastomer and solvent in the composition on the sunscreen performance. All ingredients are expressed by weight percent by the total formulation, and as level of active ingredient.

TABLE 10

| | Samples | | | |
|---|---|---|---|---|
| Ingredient | 12 | 13 | 14 | 15 |
| DC245[a] | Balance | Balance | Balance | Balance |
| Dual modified silicone elastomer/DC245 blend | 26.5 | 20.5 | 18.5 | 10.5 |

TABLE 10-continued

| Ingredient | Samples | | | |
|---|---|---|---|---|
| | 12 | 13 | 14 | 15 |
| PEG-10 dimethicone | 1.19 | 1.19 | 1.19 | 1.19 |
| Parsol MCX$^c$ | 5 | 5 | 5 | 5 |
| Parsol 1789$^e$ | 1 | 1 | 1 | 1 |
| Cholesterol | 0.20 | 0.20 | 0.20 | 0.20 |
| Stearic acid | 0.25 | 0.25 | 0.25 | 0.25 |
| Cetyl alcohol | 0.01 | 0.01 | 0.01 | 0.01 |
| Sucrose distearate | 0.13 | 0.13 | 0.13 | 0.13 |
| Water | 46.38 | 46.38 | 46.38 | 46.38 |
| Glycerine | 7.25 | 7.25 | 7.25 | 7.25 |
| Disodium EDTA | 0.05 | 0.05 | 0.05 | 0.05 |
| Potassium chloride | 1.00 | 1.00 | 1.00 | 1.00 |
| Magnesium sulfate, heptahydrate | 0.50 | 0.50 | 0.50 | 0.50 |
| Niacinamide | 3.00 | 3.00 | 3.00 | 3.00 | protocol was used to measure the viscosities and in vitro SPF values of the compositions as described in Examples 3 and 4.

Results

It can be seen that samples comprising lower amount of a blend of dual modified silicone elastomer and solvent showed higher SPF values. Sample 15 comprising 10.5% by weight of a blend of dual modified silicone elastomer and solvent showed superior sunscreen performance to other samples.

Example 7

This example demonstrates the compatibility of silicone elastomers and co-solvent caprylic/capric triglycerides (GTCC). All ingredients are expressed by weight percent by the total formulation, and as level of active ingredient.

TABLE 11

| Ingredient | Samples | | | | | | | |
|---|---|---|---|---|---|---|---|---|
| | 16 | 17 | 18 | 19 | 20 | 21 | 22 | 23 |
| DC245$^a$ | 0.27 | 0.27 | 0.84 | 0.84 | 2.84 | 2.84 | 4.84 | 4.84 |
| Dual modified silicone elastomer/DC245 blend | 26.5 | — | 26.5 | — | 26.5 | — | 26.5 | — |
| Non-functional silicone elastomer/DC245 blend | — | 26.5 | — | 26.5 | — | 26.5 | — | 26.5 |
| Caprylic/capric triglycerides | 5.07 | 5.07 | 4.0 | 4.0 | 2.0 | 2.0 | — | — |
| Caprylyl methicone | — | — | 0.5 | 0.5 | 0.5 | 0.5 | 0.5 | 0.5 |
| PEG-10 dimethicone | 1.19 | 1.19 | 1.19 | 1.19 | 1.19 | 1.19 | 1.19 | 1.19 |
| Parsol MCX$^c$ | 6 | 6 | 6 | 6 | 6 | 6 | 6 | 6 |
| Parsol 1789$^e$ | 2 | 2 | 2 | 2 | 2 | 2 | 2 | 2 |
| Cholesterol | 0.20 | 0.20 | 0.20 | 0.20 | 0.20 | 0.20 | 0.20 | 0.20 |
| Stearic acid | 0.25 | 0.25 | 0.25 | 0.25 | 0.25 | 0.25 | 0.25 | 0.25 |
| Cetyl alcohol | 0.01 | 0.01 | 0.01 | 0.01 | 0.01 | 0.01 | 0.01 | 0.01 |
| Sucrose distearate | 0.13 | 0.13 | 0.13 | 0.13 | 0.13 | 0.13 | 0.13 | 0.13 |
| Water | 46.38 | 46.38 | 46.38 | 46.38 | 46.38 | 46.38 | 46.38 | 46.38 |
| Glycerine | 7.25 | 7.25 | 7.25 | 7.25 | 7.25 | 7.25 | 7.25 | 7.25 |
| Disodium EDTA | 0.05 | 0.05 | 0.05 | 0.05 | 0.05 | 0.05 | 0.05 | 0.05 |
| Potassium chloride | 1.00 | 1.00 | 1.00 | 1.00 | 1.00 | 1.00 | 1.00 | 1.00 |
| Magnesium sulfate, heptahydrate | 0.50 | 0.50 | 0.50 | 0.50 | 0.50 | 0.50 | 0.50 | 0.50 |
| Niacinamide | 3.00 | 3.00 | 3.00 | 3.00 | 3.00 | 3.00 | 3.00 | 3.00 |
| DMDM hydantion (and) iodopropynyl butylcarbamate | 0.20 | 0.20 | 0.20 | 0.20 | 0.20 | 0.20 | 0.20 | 0.20 |
| Viscosity/cP | 130000 | 83000 | 130000 | 88000 | 160000 | 129000 | 200000 | 166000 |

TABLE 10-continued

| Ingredient | Samples | | | |
|---|---|---|---|---|
| | 12 | 13 | 14 | 15 |
| DMDM hydantion (and) iodopropynyl butylcarbamate | 0.20 | 0.20 | 0.20 | 0.20 |
| Viscosity/cP | 280000 | 129000 | 120000 | NM$^d$ |
| In vitro SPF 1 day storage | 5.57 | 5.90 | 6.31 | 11.51 |

Methods

Samples were prepared by adding different amounts of the blend of dual modified silicone elastomer and solvent (with a solid content of 14.5%) in the formulation. The same

TABLE 12

| Ingredient | Samples | | | | | |
|---|---|---|---|---|---|---|
| | 24 | 25 | 26 | 27 | 28 | 29 |
| DC245$^a$ | 3.34 | 3.34 | 1.34 | 1.34 | 1.34 | 1.34 |
| Dual modified silicone elastomer/DC245 blend | 26.5 | — | 26.5 | — | 26.5 | — |
| Non-functional silicone elastomer/DC245 blend | — | 26.5 | — | 26.5 | — | 26.5 |
| Caprylic/capric triglycerides | 2.0 | 2.0 | 4.0 | 4.0 | 2.0 | 2.0 |
| PEG-10 dimethicone | 1.19 | 1.19 | 1.19 | 1.19 | 1.19 | 1.19 |
| Parsol MCX$^c$ | 6 | 6 | 6 | 6 | 7.5 | 7.5 |
| Parsol 1789$^e$ | 2 | 2 | 2 | 2 | 2.5 | 2.5 |
| Cholesterol | 0.20 | 0.20 | 0.20 | 0.20 | 0.20 | 0.20 |
| Stearic acid | 0.25 | 0.25 | 0.25 | 0.25 | 0.25 | 0.25 |

TABLE 12-continued

| Ingredient | Samples | | | | | |
|---|---|---|---|---|---|---|
| | 24 | 25 | 26 | 27 | 28 | 29 |
| Cetyl alcohol | 0.01 | 0.01 | 0.01 | 0.01 | 0.01 | 0.01 |
| Sucrose distearate | 0.13 | 0.13 | 0.13 | 0.13 | 0.13 | 0.13 |
| Water | 46.38 | 46.38 | 46.38 | 46.38 | 46.38 | 46.38 |
| Glycerine | 7.25 | 7.25 | 7.25 | 7.25 | 7.25 | 7.25 |
| Disodium EDTA | 0.05 | 0.05 | 0.05 | 0.05 | 0.05 | 0.05 |
| Potassium chloride | 1.00 | 1.00 | 1.00 | 1.00 | 1.00 | 1.00 |
| Magnesium sulfate, heptahydrate | 0.50 | 0.50 | 0.50 | 0.50 | 0.50 | 0.50 |
| Niacinamide | 3.00 | 3.00 | 3.00 | 3.00 | 3.00 | 3.00 |
| DMDM hydantion (and) iodopropynyl butylcarbamate | 0.20 | 0.20 | 0.20 | 0.20 | 0.20 | 0.20 |
| Stability | Stable for 21 days | Stable for 14 days | Stable for 21 days | Stable for 14 days | Stable for 67 days | Stable for 2 hours |

Method

Samples were prepared by adding different blends of silicone elastomer and solvent (with a solid content of 14.5%) of the same amount in the formulation. The same protocol was used to measure the viscosities and stability of the compositions as described in Example 3.

Results

It can be seen that samples comprising dual-modified silicone elastomer showed much better compatibility with co-solvent caprylic/capric triglycerides than those comprising non-functional silicone elastomer. Sample 16 comprising GTCC in an amount higher than 5 wt % still maintained good viscosity, indicating the blend of silicone elastomer and solvent maintained its structure.

When higher amounts of sunscreen agents were added into the compositions, samples comprising dual modified silicone elastomer showed much better compatibility with co-solvent caprylic/capric triglycerides than those comprising non-functional silicone elastomer. Sample 28 was stable for 67 days while Sample 29 became unstable after 2 hours.

The invention claimed is:

1. A sunscreen composition comprising:
   (i) a blend of silicone elastomer and solvent; and
   (ii) a cosmetically acceptable carrier;
   wherein the solvent is a volatile silicone oil selected from octamethylcyclotetrasiloxane, decamethylcyclopentasiloxane, dodecamethylcyclohexasiloxane, blends of methyl trimethicone and dimethicone and mixtures thereof; and
   wherein the silicone elastomer has the chemical structure of formula I, wherein:
   each $R_1$ is independently $C_{4-36}$ alkyl chain;
   each $R_2$ is independently phenyl or $CH_3$;
   each $R_3$ is independently phenyl; and
   each x is independently an integer from 3 to 100; each y is independently an integer from 1 to 100; each z is independently an integer from 1 to 100; each m is independently an integer from 1 to 100; and
   each n is independently an integer from 4 to 1000

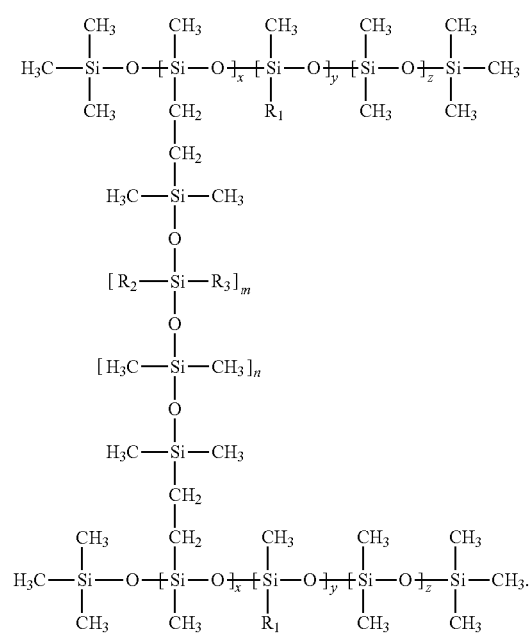

Compound of Formula I

2. The composition as claimed in claim 1 further comprising 0.1 to 30% by weight of an organic sunscreen agent.

3. The composition as claimed in claim 1 wherein the composition is substantially free of an organic sunscreen agent.

4. The composition as claimed in claim 2 comprising 0.1 to 10% by weight of organic sunscreen agent wherein the agent is a UV-A sunscreen agent.

5. The composition as claimed in claim 2 comprising 0.1 to 20% by weight of organic sunscreen agent wherein the agent is a UV-B sunscreen agent.

6. The composition as claimed in claim 1 wherein the volatile silicone oil is decamethylcyclopentasiloxane.

7. The composition as claimed in claim 1 wherein the $R_1$ of the silicone elastomer is a $C_{12}$ alkyl group.

8. The composition as claimed in claim 1 wherein the $R_2$ of the silicone elastomer is a phenyl group.

9. The composition as claimed in claim 1 wherein the alkyl mole content of the silicone elastomer is from 0.01 to 0.99.

10. The composition as claimed in claim 1 wherein the phenyl mole content of the silicone elastomer is from 0.01 to 0.50.

11. The composition as claimed in claim 1 wherein the blend of silicone elastomer and solvent comprises silicone elastomer in an amount of from 1 to 70% by weight of the blend.

12. The composition as claimed in claim 1 wherein the blend of silicone elastomer and solvent comprises the silicone elastomer and the solvent in a weight ratio from 1:20 to 2:1.

13. The composition as claimed in claim 1 wherein the composition comprises the blend of silicone elastomer and solvent in an amount of from 0.1 to 60% by weight of the total composition.

14. The composition as claimed in claim 1 wherein the composition further comprises an emollient oil.

15. A method for providing skin care benefit comprising the step of topically applying the personal care composition as claimed in claim 1 to the skin of an individual in need thereof.

16. A sunscreen composition according to claim 1 wherein:
 each x is independently an integer from 3 to 20;
 each y is independently an integer from 1 to 20;
 each z is independently an integer from 6 to 50;
 each m is independently an integer from 5 to 30; and
 each n is independently an integer from 40 to 500.

\* \* \* \* \*